US006651656B2

(12) United States Patent
Demers et al.

(10) Patent No.: US 6,651,656 B2
(45) Date of Patent: Nov. 25, 2003

(54) METHOD AND APPARATUS FOR NON-INVASIVE BREATHING ASSIST

(75) Inventors: Jason A. Demers, Manchester, NH (US); David McGill, Bedford, NH (US)

(73) Assignee: Deka Products Limited Partnership, Manchester, NH (US)

(*) Notice: Subject to any disclaimer, the term of this patent is extended or adjusted under 35 U.S.C. 154(b) by 0 days.

(21) Appl. No.: 09/867,128

(22) Filed: May 29, 2001

(65) Prior Publication Data

US 2002/0179088 A1 Dec. 5, 2002

(51) Int. Cl.[7] ........................ A61M 16/00; A61B 5/087; A62B 7/00

(52) U.S. Cl. ............................ 128/204.18; 128/204.22; 128/204.23; 128/204.26

(58) Field of Search ........................ 128/204.18, 204.21, 128/204.22, 204.23, 204.26, 204.29, 204.24, 898

(56) References Cited

U.S. PATENT DOCUMENTS

| | | | | | |
|---|---|---|---|---|---|
| 4,737,624 | A | | 4/1988 | Schwarte | |
| 5,056,513 | A | | 10/1991 | Boutin | |
| 5,284,133 | A | | 2/1994 | Burns et al. | |
| 5,549,106 | A | * | 8/1996 | Gruenke et al. | 128/204.21 |
| 5,660,171 | A | * | 8/1997 | Kimm et al. | 128/204.21 |
| 5,915,381 | A | * | 6/1999 | Nord | 128/204.18 |
| 5,970,975 | A | * | 10/1999 | Estes et al. | 128/204.18 |
| 6,105,575 | A | * | 8/2000 | Estes et al. | 128/204.21 |
| 6,173,711 | B1 | * | 1/2001 | Ruton | 128/204.25 |
| 6,213,119 | B1 | * | 4/2001 | Brydon et al. | 128/204.18 |
| 6,220,244 | B1 | * | 4/2001 | McLaughlin | 128/204.18 |
| 6,240,921 | B1 | * | 6/2001 | Brydon et al. | 128/204.18 |
| 6,247,470 | B1 | * | 6/2001 | Ketchedjian | 128/200.28 |
| 6,269,811 | B1 | * | 8/2001 | Duff et al. | 128/204.18 |
| 6,318,366 | B1 | * | 11/2001 | Davenport | 128/204.18 |
| 6,332,463 | B1 | * | 12/2001 | Farrugia et al. | 128/204.18 |
| 6,378,520 | B1 | * | 4/2002 | Davenport | 128/204.18 |
| 2002/0017300 | A1 | * | 2/2002 | Hickle et al. | 128/204.22 |

FOREIGN PATENT DOCUMENTS

| | | |
|---|---|---|
| GB | 0 661 071 A1 | 7/1995 |
| WO | WO 01/95971 A2 | 12/2001 |

* cited by examiner

*Primary Examiner*—Henry Bennett
*Assistant Examiner*—Kathryn Ferko
(74) *Attorney, Agent, or Firm*—Bromberg & Sunstein LLP

(57) ABSTRACT

An apparatus, method and system for non-invasive breathing assistance to a patient. The apparatus comprises a hose or other gas conduit with a valve. Proximity of the patient to a sensor causes the valve to open, directing a pressurized stream of air or other gas at the patient's mouth, assisting the patient in breathing.

7 Claims, 3 Drawing Sheets

ANGLED VIEW

METHOD AND APPARATUS FOR NON-INVASIVE BREATHING ASSIST

FIELD OF THE INVENTION

This invention relates to an apparatus, method and system for assisting a patient's breathing and, more particularly, for assisting breathing without contacting the patient.

BACKGROUND OF THE INVENTION

Patients with diseases that involve muscular degeneration, such as amyotrophic lateral sclerosis (also known as Lou Gehrig's disease), frequently require assistance in breathing. Such assistance typically takes the form of forcibly inflating and deflating the patient's lungs using breathing masks or endo-tracheal tubes connected to pumps. Such methods are invasive, interfering with other functions such as speech. Further, such methods provide continuous intervention in the breathing process, even when the patient requires only intermittent assistance to catch his or her breath. An impediment for implementing breathing assistance on-demand by the patient is that patients with such degenerative muscular diseases often do not have use of their limbs to turn such breathing assistance on and off.

SUMMARY OF THE INVENTION

In accordance with preferred embodiments of the present invention, a system is provided for directing a pressurized stream of gas at a patient's mouth to assist in breathing. The system includes a source of the gas stream; a conduit for conveying the stream from an inlet, connected to the gas source, to an outlet directing the stream toward the patient's mouth; a sensor for detecting a respiratory need of the patient; a valve inserted in the conduit for controlling the stream; and a controller for controlling the valve, actuated based on the respiratory need of the patient.

In accordance with a further embodiment of the invention, a device is provided for directing a pressurized stream of gas at a patient's mouth to assist in breathing. The device includes a conduit for conveying the gas stream from an inlet, connected to a gas source, to an outlet directing the stream toward the patient's mouth; a sensor for detecting a respiratory need of the patient; a by-pass vent for venting the stream when breathing assistance is not required; a valve inserted in the conduit for dividing the stream between the outlet and the vent; and a controller for controlling the valve that is actuated based on the respiratory need of the patient.

In accordance with a further embodiment of the invention, a method is provided for directing a pressurized stream of a gas at a patient's mouth to assist in breathing. The method comprises sensing a respiratory need of the patient; controlling a flow of the stream based on the respiratory need of the patient; and directing the stream toward a vicinity of the patient's mouth.

DETAILED DESCRIPTION OF SPECIFIC EMBODIMENTS

The present invention advantageously addresses the cited problems with breathing assistance systems for patients with diseases involving muscular degeneration. The need for an invasive mask or other device connected to the patient's airway is eliminated and patient control of breathing assistance is facilitated.

Figure 1:
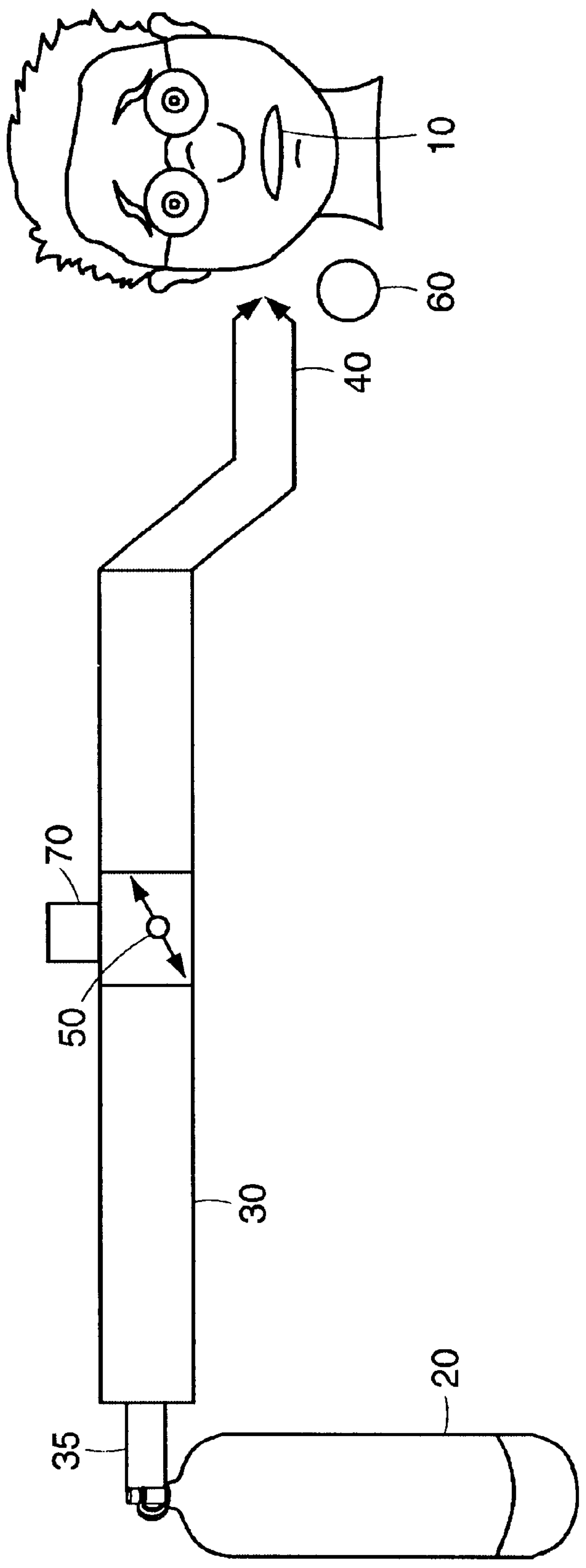
FIG. 1 shows a sectional side view of one embodiment of the present invention.

FIG. 1 shows a sectional side view of one embodiment of the present invention which directs a pressurized stream of gas at a patient's mouth 10. A source 20 of a stream of pressurized gas, such as a pump or a pressurized gas cylinder or a fan, is provided. The gas may be atmospheric air or an air-oxygen mixture, or another gas. The gas source 20 is coupled to a conduit 30 via an inlet 35 so that gas may be introduced into the conduit. The conduit conveys the gas to an outlet 40, such as a nozzle. The term "conduit" as used in this description and in any appended claims, will be understood to include any element that functions as a channel that conveys gas, including, without limitation, a hose, a tube and a pipe. The outlet directs the stream of gas at the patient's mouth 10. A valve 50 in the conduit modulates the stream of gas including varying the flow rate or pressure and additionally turning the flow off and on. A sensor 60 senses a respiratory need of the patient and signals a controller 70 typically via an electromagnetic channel. Such sensors 60 may include, for example without limitation, a microswitch triggered by contact with the patient's mouth or another part of the patient's body or an infrared detector that detects proximity of the patient's head or a motion sensor that detects movement of the patients. When the controller 70 receives the signal from the sensor 60 indicating the patient's respiratory need, the controller opens the valve, either partially or fully, thereby directing the pressurized stream of gas at the patient's mouth, providing assistance in inflating the patient's lungs.

Figure 3A:
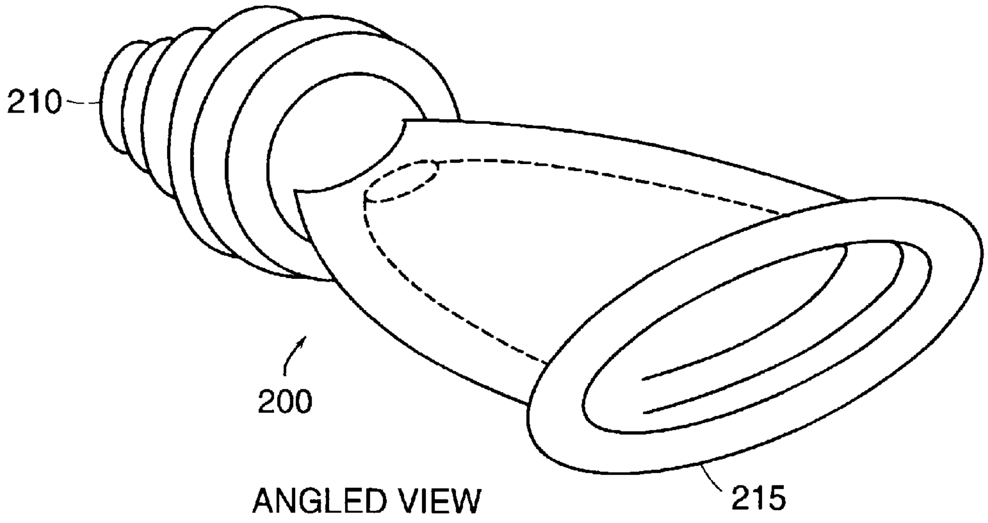
FIG. 3*a* shows an angle view of a nozzle in an embodiment of the present invention.
Figure 3B:
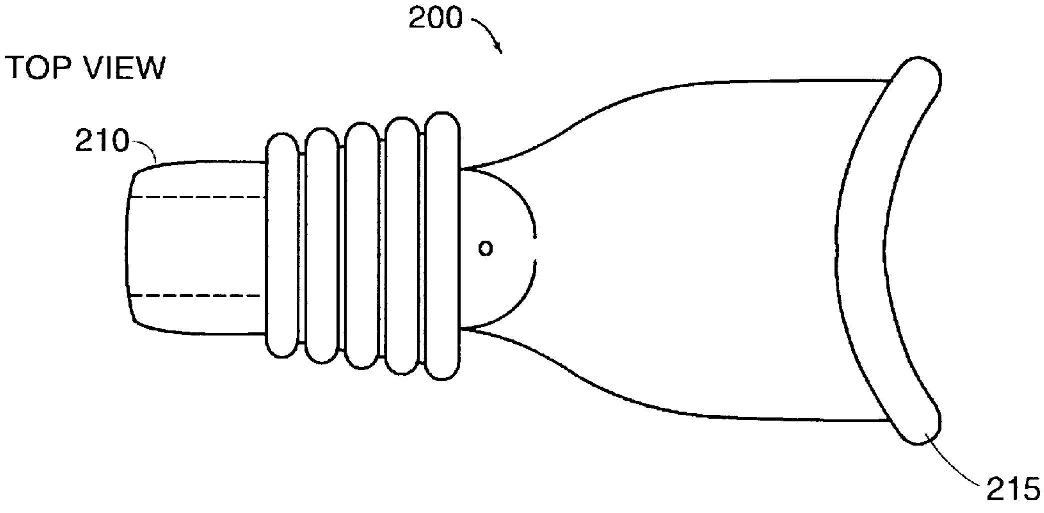
FIG. 3*b* shows a top view of the nozzle in an embodiment of the present invention.

As an illustrative example, for a patient with Lou Gehrig's disease, a rotary blower pump generates a continuous gas stream of approximately 3.5 liters per second at a pressure of up to 60 inches of water. A nozzle, as the conduit outlet, directs the gas stream at the patient's mouth. FIG. 3*a* shows an angle view of the nozzle 200, which is made of plastic. A first end of the nozzle 210 mates with the conduit, while the other end 215 directs gas at the patient. FIG. 3*b* shows a top view of the nozzle. With the nozzle positioned two to three inches from the patient's mouth, the stream of gas provides mechanical assistance to the patient in inflating the patient's lungs, when the stream is turned on. The proximity of the patient's face to a diffuse, reflective infrared sensor, such as an Omron E3C-C, positioned 10 to 50 mm from the patient's face, signals the device to turn on the gas stream.

Figure 2:
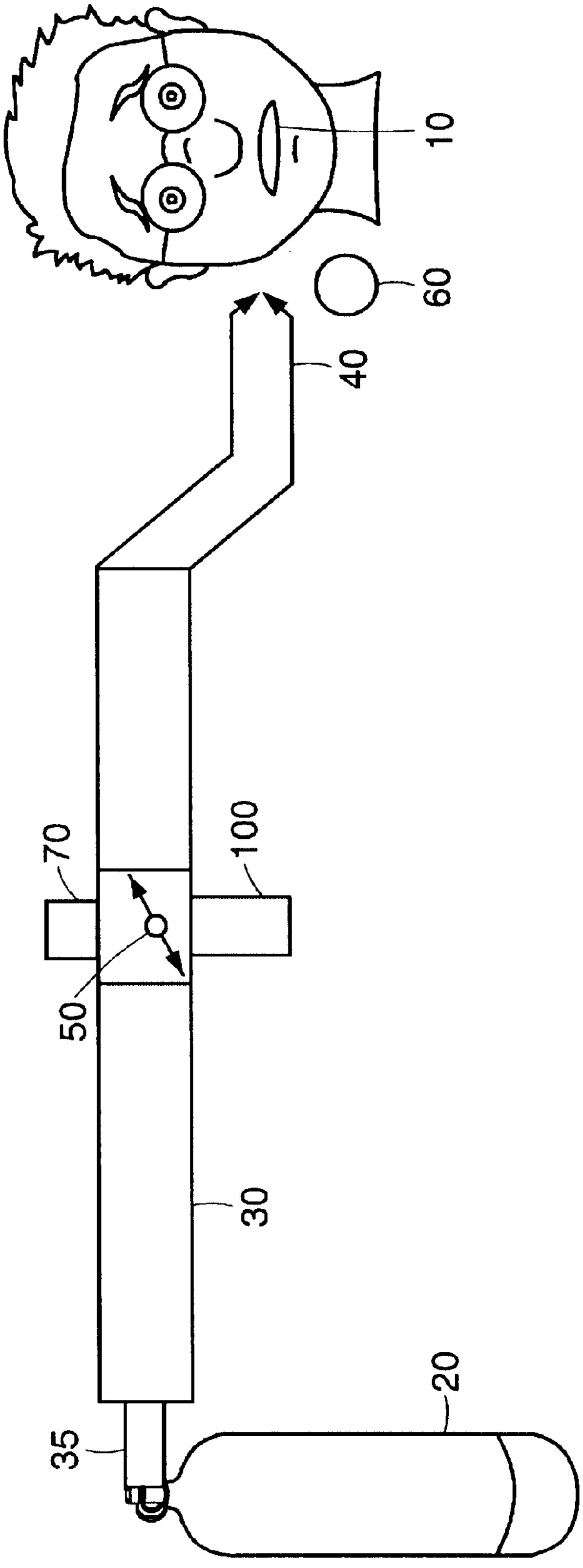
FIG. 2 shows a sectional side view of another embodiment of the present invention.

FIG. 2 shows another preferred embodiment of the invention. This embodiment further comprises a by-pass vent 100 inserted in the conduit 30. The valve 50 divides the gas stream between the outlet 40 and the by-pass vent 100. This arrangement allows the gas source 20, if, for example, it is a pump, to supply a continuous stream of gas, thus extending the life of the pump. The valve 50 and by-pass vent 100 may be located in the conduit near the gas source, remote from the outlet 40, to reduce noise and any disturbance to the patient from the gas stream emitted by the by-pass vent 100.

Having thus described various illustrative embodiments of the present invention, some of its advantages and optional features, it will be apparent that such embodiments are presented by way of example only and not by way of limitation. Those skilled in the art could readily devise alterations and improvements on these embodiments, as well as additional embodiments, without departing from the spirit and scope of the invention. All such modifications are within the scope of the invention as claimed.

What is claimed is:

1. A device for directing a pressurized stream of gas from a gas source toward a patient having a mouth, the device comprising:

a. an inlet to receive gas from the source;

b. an outlet for directing the stream toward a vicinity of the patient's mouth;

c. a conduit for delivering the stream from the inlet to the outlet;

d. a sensor for detecting a respiratory need of the patient, the sensor generating a signal based on the respiratory need;

e. a valve inserted in the conduit for controlling the stream; and f. a controller for controlling the valve, the controller connected to the sensor, the controller actuated based on the signal, wherein the device is capable of operation with the device not contacting the patient.

2. A device according to claim 1, wherein the sensor detects the respiratory need through proximity of the patient to the sensor.

3. A device according to claim 1, wherein the sensor is a switch.

4. A device for directing a pressurized stream of gas from a gas source toward a patient having a mouth, the device comprising:

a. an inlet to receive gas from the source;

b. an outlet for directing the stream toward a vicinity of the patient's mouth;

c. a conduit for delivering the stream from the inlet to the outlet;

d. a by-pass vent inserted in the conduit;

e. a sensor for detecting a respiratory need of the patient, the sensor generating a signal based on the respiratory need;

f. a valve inserted in the conduit for dividing the stream between the outlet and the vent; and g. a controller for controlling the valve, the controller connected to the sensor, the controller actuated based on the signal, wherein the device is capable of operation with the device not contacting the patient.

5. A device according to claim 4, wherein the sensor detects the respiratory need through proximity of the patient to the sensor.

6. A device according to claim 4, wherein the sensor is a switch.

7. A system for directing a pressurized stream of a gas toward a patient having a mouth to assist in breathing, the system comprising:

a. a source of the stream;

b. an inlet to receive the gas from the source;

c. an outlet for directing the stream toward a vicinity of the patient's mouth;

d. a conduit for conveying the stream from the inlet to the outlet;

e. a sensor for detecting a respiratory need of the patient, the sensor generating a signal based on the respiratory need;

f. a valve inserted in the conduit for controlling the stream; and g. a controller for controlling the valve, the controller connected to the sensor, the controller actuated based on the signal, wherein the device is capable of operation with the device not contacting the patient.

* * * * *